(12) United States Patent
Kiel

(10) Patent No.: US 9,925,128 B1
(45) Date of Patent: Mar. 27, 2018

(54) SKIN COLORED ANTIPERSPIRANT DEODORANT

(71) Applicant: Donna Marie Kiel, Seatac, WA (US)

(72) Inventor: Donna Marie Kiel, Seatac, WA (US)

( * ) Notice: Subject to any disclaimer, the term of this patent is extended or adjusted under 35 U.S.C. 154(b) by 406 days.

(21) Appl. No.: 14/140,517

(22) Filed: Dec. 25, 2013

Related U.S. Application Data

(60) Provisional application No. 61/827,786, filed on May 28, 2013.

(51) Int. Cl.
*A61K 8/02* (2006.01)
*A61Q 15/00* (2006.01)
*A45D 40/04* (2006.01)

(52) U.S. Cl.
CPC ............ *A61K 8/0229* (2013.01); *A45D 40/04* (2013.01); *A61Q 15/00* (2013.01)

(58) Field of Classification Search
CPC ............ A61K 8/0229; A61K 2800/26; A61K 2800/262; A61K 2800/42; A61K 2800/43; A61K 2800/436; A61K 2800/437; A61Q 15/00; A45D 40/04; A45D 2040/0012; A45D 2040/0025
See application file for complete search history.

(56) References Cited

U.S. PATENT DOCUMENTS

| | | | |
|---|---|---|---|
| 5,254,332 A * | 10/1993 | Grezcyn | A61K 8/0229 424/65 |
| 5,449,511 A | 9/1995 | Coe | |
| 5,492,691 A | 2/1996 | Bahr et al. | |
| 5,500,209 A | 3/1996 | Ross et al. | |
| 5,597,556 A * | 1/1997 | Moghe | A61K 8/0229 424/65 |
| 5,718,865 A * | 2/1998 | Askew | A61K 8/0229 264/239 |
| 6,835,374 B2 | 12/2004 | Parekh et al. | |
| 8,293,218 B2 | 10/2012 | Rosa et al. | |
| 8,309,064 B2 | 11/2012 | Rosa et al. | |
| 2002/0141957 A1* | 10/2002 | Tan | A61K 8/26 424/63 |
| 2004/0187885 A1* | 9/2004 | Strong | A45D 40/18 132/301 |
| 2008/0152418 A1* | 6/2008 | Maddy | A45D 40/00 401/61 |
| 2011/0150555 A1* | 6/2011 | Yarlagadda | A45D 40/04 401/52 |
| 2012/0009135 A1* | 1/2012 | Misner | A45D 40/16 424/65 |
| 2012/0114582 A1* | 5/2012 | Batchelor | A61K 8/19 424/65 |
| 2012/0244099 A1 | 9/2012 | Gale et al. | |
| 2014/0335029 A1* | 11/2014 | Rudolph | A01N 37/36 424/55 |

OTHER PUBLICATIONS

Pantone 2014 Catalog, 2014, USA.

* cited by examiner

*Primary Examiner* — Michael B. Pallay
(74) *Attorney, Agent, or Firm* — Albert Bordas, P.A.

(57) ABSTRACT

A deodorant stick having a color component as skin-tone pigmentation, for the discreet wearing of deodorant. The color component matches a color of user's human skin, acting as camouflage that changes its color as it is applied on the skin to match the skin. The deodorant stick includes a plastic casing, containing an interior plastic casing where the interior casing contains a skin-color pigmented deodorant, a fitted plastic cover, a plastic wheel mechanism, and a set of rubber-based grips. The fitted plastic cover may be transparent or of a color that matches the color component included in the deodorant stick. The rubber-based grips matches the color of the color component included in the deodorant stick.

1 Claim, 4 Drawing Sheets

SKIN COLORED ANTIPERSPIRANT DEODORANT

CLAIM OF PRIORITY FROM RELATED APPLICATIONS

The present application claims priority from U.S. Provisional Patent Application No. 61/827,786 filed on May 28, 2013 to Donna Kiel from Hazelwood, MO (U.S.A) directed to a COLOR ME DRY, that is hereby incorporated by reference.

BACKGROUND OF THE INVENTION

Field of the Invention

The inventive device object of the present application generally relates to deodorants and more specifically to a deodorant with human skin-tone pigmentation.

Brief Description of the Prior Art

Women feel confident when they know they are looking their best. Women like to dress comfortably, and for many that means sleeveless blouses and dresses. Many times women like to wear sexy lingerie and slinky loungewear which can be sleeveless as well. Men and women wearing swimsuits on vacations, around indoor swimming pools and during warm weather want to know they look as good as possible when wearing their swimsuits.

This creates a "conflict" in the sense that if one is wearing underarm deodorant the color of the deodorant may tell out that the person is wearing it and may make the individual feel ashamed. Even if we assume that there is nothing to be ashamed in wearing deodorant it may look dirty, inconvenient and not classy. From there the need of a deodorant that may match the color of one's skin.

Camouflaged deodorants are well known in the art. Various Patents and Published Patent applications are in fact directed to deodorants and antiperspirants with skin tones. While developing the invention of the instant application independently the Inventor researched extensively the public record as well as the current market for spittoons and the most relevant examples found in the search are mentioned in the Information Disclosure Statement (IDS) attached from anything on today's market.

SUMMARY OF THE INVENTION

The invention is a deodorant stick with skin-tone pigmentation, for the discreet wearing of deodorant. It is then the principal object of the present invention to provide a skin-colored deodorant, allowing the user to surreptitiously wear deodorant with clothing which bares one's arms. The inventor commonly refers to the skin-colored deodorant of the present application as the Color Me Dry.

It is a secondary objective of the present invention to provide a device that will allow the user to quickly and efficiently apply deodorant to their underarms. It is an additional objective of the present invention to provide a device that does not deteriorate over time and it is generally tolerated by human skin. It is a final objective of the present invention to provide for a device that is inexpensive to build, but that can eventually be sold at a premium.

These and other objective achieved by the device of the present invention will be apparent by the drawings, by their detailed description, and by the specification here from appended.

DESCRIPTION OF THE PREFERRED EMBODIMENT

Figure 1:
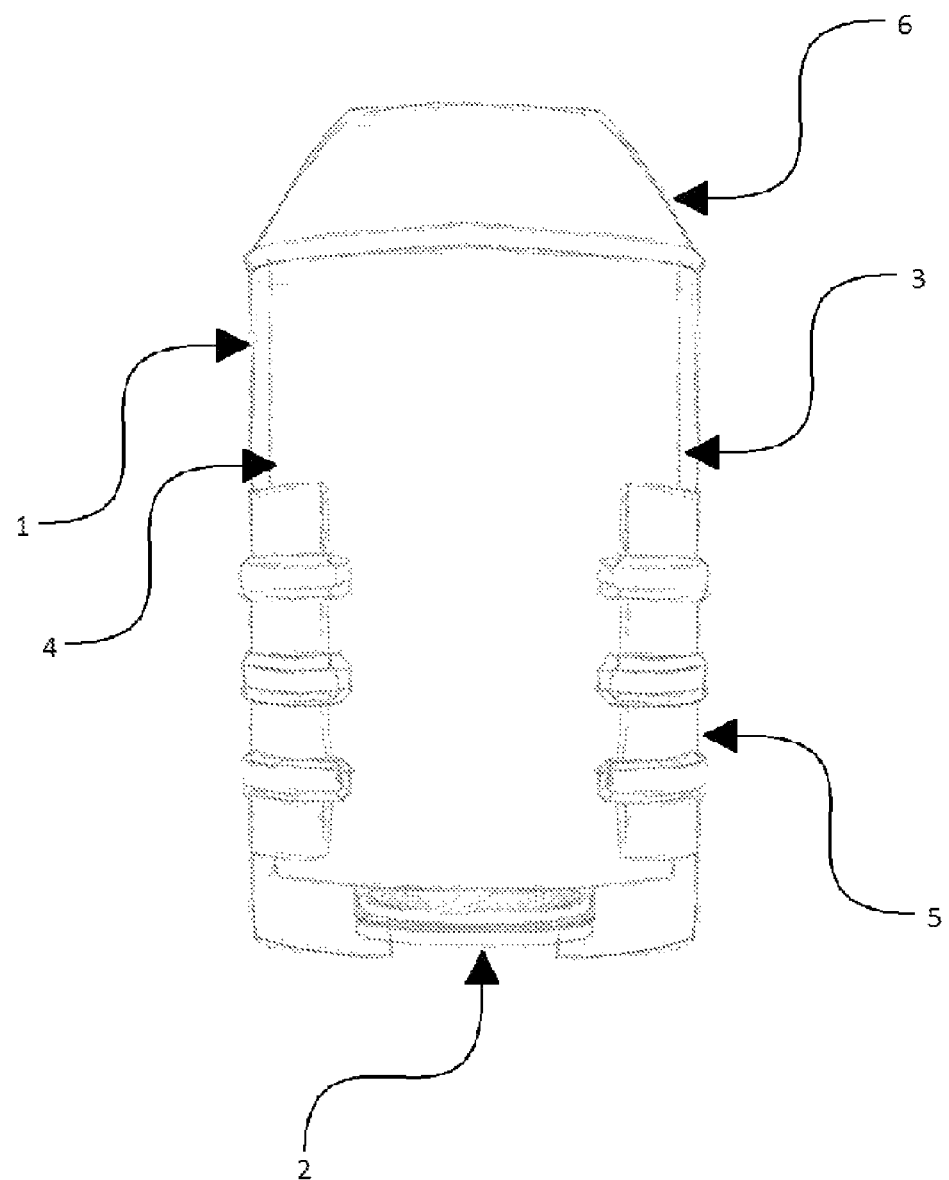
FIG. 1 shows a front elevation view of one of the preferred embodiments of the skin-colored deodorant device of the present application.
Figure 2:
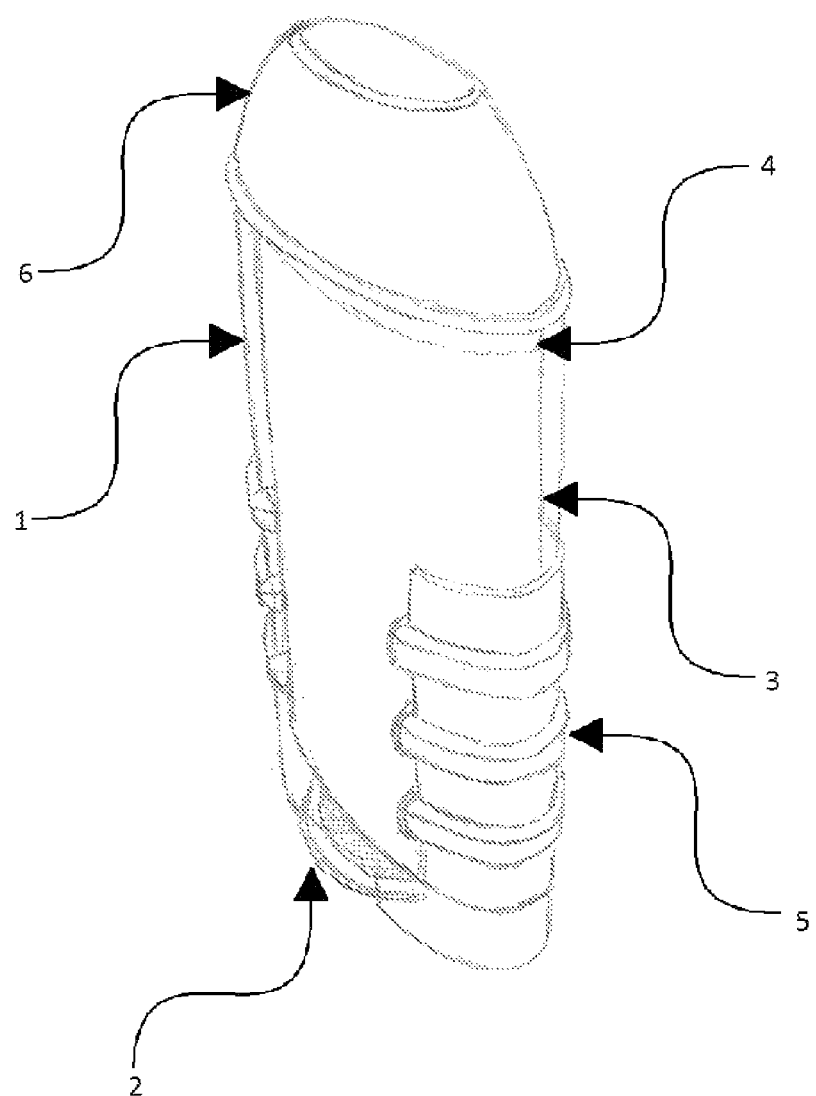
FIG. 2 is a top perspective view of the skin-colored deodorant device of FIG. 1.
Figure 3:
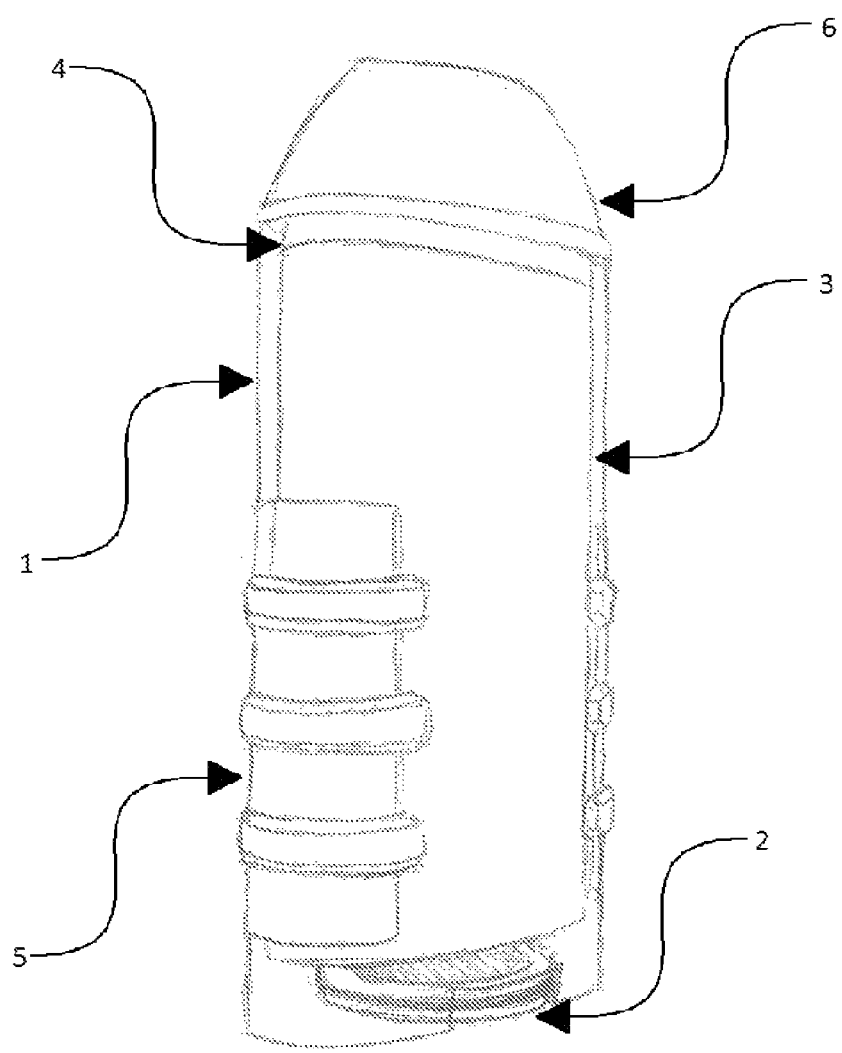
FIG. 3 is bottom perspective view of the skin-colored deodorant device of FIG. 1.
Figure 4:
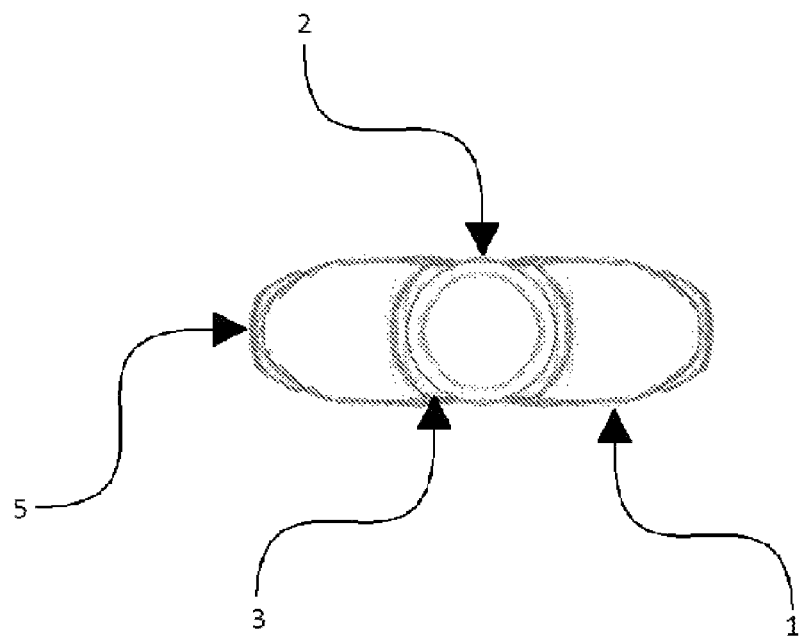
FIG. 4 is bottom view of the skin-colored deodorant device of FIG. 1

The invention is a deodorant stick, with skin-tone pigmentation, for the discreet wearing of deodorant. As it can be inferred from the drawings essential elements of the skin-colored deodorant device of the present application include: One outer plastic casing (1), containing a plastic wheel (2) connected to an interior plastic casing (3) holding skin-colored deodorant (4), rubber grips (5), and a plastic cap (6).

A skin-colored deodorant stick (4) contained in plastic casings (1,3) with a plastic cap (6) confers an efficient way for the user to transport and store the skin-colored deodorant (4). These plastic casings (1,3) contain a plastic wheel (2) for vertically pushing the skin-colored deodorant (4) when depleted, and rubber grips (5) for efficiently grasping the outer plastic casing (1). Included with the skin-colored deodorant (4) is a fitted plastic cap (6) situated above the outer plastic casing (1) for preventing deterioration and/or erosion to the contained skin-colored deodorant (4). The Color Me Dry is designed to be stored in a bathroom cupboard or the like, but it could also be transported as necessary.

Depending on the desired color of the device, darker or lighter-colored models of the skin-colored deodorant (4) may be made. Components for said skin-colored deodorant (4) include but are not limited to aluminium chloride, aluminium chlorohydrate, aluminium-zirconium compounds, and other common antiperspirant/deodorant compounds.

Human skin color ranges in variety from the darkest brown to the lightest pinkish-white hues. Human skin pigmentation is the result of natural selection. Skin pigmentation in human beings evolved to primarily regulate the amount of ultraviolet radiation penetrating the skin, controlling its biochemical effects.

The actual skin color of different humans is affected by many substances, although the single most important substance determining human skin color is the pigment melanin. Melanin is produced within the skin in cells called melanocytes and it is the main determinant of the skin color of darker-skinned humans. The skin color of people with light skin is determined mainly by the bluish-white connective tissue under the dermis and by the haemoglobin circulating in the veins of the dermis. The red color underlying the skin becomes more visible, especially in the face, when, as consequence of physical exercise or the stimulation of the nervous system (anger, fear), arterioles dilate.

There is a correlation between the geographic distribution of UV radiation (UVR) and the distribution of indigenous skin pigmentation around the world. Areas that highlight higher amounts of UVR reflect darker-skinned populations, generally located nearer towards the equator. Areas that are far from the tropics and closer to the poles have lower concentration of UVR, which is reflected in lighter-skinned populations. Researchers suggest that human populations over the past 50,000 years have changed from dark-skinned to light-skinned and vice versa as they migrated to different UV zones, and that such major changes in pigmentation may have happened in as little as 100 generations (~2,500 years) through selective sweeps. Natural skin color can also darken as a result of tanning due to exposure to sunlight. The leading theory is that skin color adapts to intense sunlight irradiation to provide partial protection against the ultraviolet fraction that produces damage and thus mutations in the DNA of the skin cells.

In addition, it has been observed that adult human females are considerably lighter in skin pigmentation than males. Females need more calcium during pregnancy and lactation. The body synthesizes vitamin D from sunlight, which helps it absorb calcium. Females evolved to have lighter skin so their bodies absorb more calcium.

Matching one's skin color is a challenging task not only due to the wide variety of skin tones but also to seasonal and periodic variations on one's skin. It is possible to catalog the entire range of human skin tones—to create a "chromatic inventory" of all humankind. This can be done for example by photographing a subject, taking an 11×11 pixel "sample" of that person's skin from the resulting image, and matching it to one of the thousands of colors in Pantone's international color database. Pantone colors are a standard used by the design industry. Then fill the background of the picture with that Pantone, and lists the alphanumeric code the company has assigned that particular shade.

Pantone Inc. is a corporation headquartered in Carlstadt, N.J. The company is best known for its Pantone Matching System (PMS), a proprietary color space used in a variety of industries, primarily printing, though sometimes in the manufacture of colored paint, fabric, and plastics.

The company's primary products include the Pantone Guides, which consist of a large number of small (approximately 6×2 inches or 15×5 cm) thin cardboard sheets, printed on one side with a series of related color swatches and then bound into a small "fan deck". For instance, a particular "page" might contain a number of yellows of varying tints.

The idea behind the PMS is to allow designers to "color match" specific colors when a design enters production stage, regardless of the equipment used to produce the color. This system has been widely adopted by graphic designers and reproduction and printing houses. Pantone recommends that PMS Color Guides be purchased annually, as their inks become yellowish over time. Color variance also occurs within editions based on the paper stock used (coated, matte or uncoated), while interedition color variance occurs when there are changes to the specific paper stock used.

The Pantone Color Matching System is largely a standardized color reproduction system. By standardizing the colors, different manufacturers in different locations can all refer to the Pantone system to make sure colors match without direct contact with one another.

Pantone colors are described by their allocated number (typically referred to as, for example, "PMS 130"). PMS colors are almost always used in branding and have even found their way into government legislation and military standards (to describe the colors of flags and seals). Pantone asserts that their lists of color numbers and pigment values are the intellectual property of Pantone and free use of the list is not allowed; however, copyright law does not support such a claim. This is frequently held as a reason why Pantone colors cannot be supported in Open Source software such as GNU Image Manipulation Program (GIMP) and are not often found in low-cost software. Pantone palettes supplied by printer manufacturers can be obtained freely, and, depending on supplier, do not come with usage restrictions beyond a sales ban on hard copies of the palette.

In a first preferred embodiment of the present application what is claimed is a composition for a deodorant further comprising a coloring agent where said color agent is provided in different tones matching the color tones of the human skin. When using this first preferred embodiment the user may check the color of the deodorant either via a transparent window in its casing or via a colored tag representing the color of the inner content affixed outside the deodorant box, or just by applying a sample on its skin. It is important to understand that the user may not necessarily choose the exact color of its skin, rather can pick the color he or she prefer.

Deodorants are classified and regulated as cosmetics by the U.S. Food and Drug Administration (FDA) and are designed to eliminate odor. Deodorants are usually alcohol-based. Alcohol initially stimulates sweating, but may also temporarily kill bacteria. Deodorants can be formulated with other, more persistent antimicrobials such as triclosan, or with metal chelant compounds that slow bacterial growth. Deodorants may contain perfume fragrances or natural essential oils intended to mask the odor of perspiration.

Deodorants combined with antiperspirant agents are classified as drugs by the FDA. Antiperspirants attempt to stop or significantly reduce perspiration and thus reduce the moist climate in which bacteria thrive. Aluminium chloride, aluminium chlorohydrate, and aluminium-zirconium compounds, most notably aluminium zirconium tetrachlorohydrex gly and aluminium zirconium trichlorohydrex gly, are frequently used in antiperspirants. Aluminium chlorohydrate and aluminium zirconium tetrachlorohydrate gly are the most frequent active ingredients in commercial antiperspirants.

Aluminium-based complexes react with the electrolytes in the sweat to form a gel plug in the duct of the sweat gland. The plugs prevent the gland from excreting liquid and are removed over time by the natural sloughing of the skin. The metal salts work in another way to prevent sweat from reaching the surface of the skin: the aluminium salts interact with the keratin fibrils in the sweat ducts and form a physical plug that prevents sweat from reaching the skin's surface. Aluminium salts also have a slight astringent effect on the pores; causing them to contract, further preventing sweat from reaching the surface of the skin. The blockage of a large number of sweat glands reduces the amount of sweat produced in the underarms, though this may vary from person to person.

Over-the-counter products labeled as "natural deodorant crystal" containing the chemical potassium alum have gained new-found popularity as an alternative health product, in spite of concerns about their contact dermatitis. A popular alternative to modern commercial deodorants is ammonium alum, which is a common type of alum sold in crystal form and often referred to as a deodorant crystal.

In a separate preferred embodiment of the present application the color compound acting as camouflages that changes its color as it is applied on the skin to match the skin underneath. One way of doing it is by dispersing in the colorless antiperspirant deodorant gel composition a finely grinded metal like powder so that it reflects the color itself of the skin. In a third preferred embodiment of the present application the deodorant composition is matched with a color that is not related to the color of the skin rather is worn and used as a fashion statement.

A a deodorant stick including a color component: where the color of said color component is either related (to), unrelated (to) or matching the color of human skin. Alternatively the color compound acting as camouflages that changes its color as it is applied on the skin to match the skin underneath.

The deodorant stick for matching the skin color of a user may be contained into a plastic casing; containing another interior plastic casing; where said interior casing contains a skin-color pigmented deodorant. Said plastic casing may include a fitted plastic cover that may either be transparent or matching the color of the color component included in said deodorant stick.

The container for the deodorant stick for matching the skin color of a user may further comprise a plastic wheel mechanism and or a set of rubber-based grips that may match the color of the color component included in said deodorant stick.

It is understood that the same consideration and embodiments made for a deodorant above can be extended to an antiperspirant. As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A deodorant, comprising:
   A) an alcohol based colorless antiperspirant deodorant gel to temporarily kill bacteria comprising aluminium chloride, aluminium chlorohydrate, aluminium-zirconium compounds including aluminium zirconium tetrachlorohydrex gly and aluminium zirconium trichlorohydrex gly, and antiperspirant and deodorant compounds, said alcohol based colorless antiperspirant deodorant gel comprising finely grinded metallic powder to reflect and match a color of human skin wearing said alcohol based colorless antiperspirant deodorant gel, said alcohol based colorless antiperspirant deodorant gel further comprising antimicrobials including triclosan, or metal chelant compounds to slow bacterial growth, said alcohol based colorless antiperspirant deodorant gel further comprising perfume fragrances to mask odor; and
   B) an applicator comprising one outer plastic casing containing a plastic wheel connected to an interior plastic casing, said outer plastic casing comprising a first transparent window to view said alcohol based colorless antiperspirant deodorant gel, said applicator further comprises rubber grips positioned on said outer plastic casing, and a plastic cap, said plastic cap is situated above said outer plastic casing for preventing deterioration of said alcohol based colorless antiperspirant deodorant gel and comprises a second transparent window to view said alcohol based colorless antiperspirant deodorant gel.

* * * * *